United States Patent
Hwu et al.

(10) Patent No.: US 6,526,121 B1
(45) Date of Patent: Feb. 25, 2003

(54) APPARATUS AND METHOD FOR IMAGING AN OBJECT WITH REAL-TIME RESPONSE

(76) Inventors: Yeu-Kuang Hwu, 4 Fl., No. 12, Aly, 4, Ln. 356 Yenshow Street, Tapai (TW); Jung Ho Je, Gyo-Soo Apt., 9-1403, Jigok-Dong, Nam-Ku, Pohang -City 790-390 (KR); Giorgio Margaritondo, Route du Signal 21, CH-1018 Lausanne (CH)

( * ) Notice: Subject to any disclaimer, the term of this patent is extended or adjusted under 35 U.S.C. 154(b) by 0 days.

(21) Appl. No.: 09/537,628

(22) Filed: Mar. 29, 2000

(51) Int. Cl.[7] .................................................. G21K 1/00
(52) U.S. Cl. .......................... 378/62; 378/98.9; 378/82
(58) Field of Search .......................... 378/62, 43, 98.9, 378/156, 98.8, 82

(56) References Cited

U.S. PATENT DOCUMENTS

| | | | | |
|---|---|---|---|---|
| 4,945,552 A | * | 7/1990 | Ueda et al. | 378/98.11 |
| 5,132,994 A | * | 7/1992 | Kato | 378/43 |
| 5,850,425 A | * | 12/1998 | Wilkens | 378/85 |
| 5,881,126 A | | 3/1999 | Momose | 378/36 |
| 6,018,564 A | | 1/2000 | Wilkins | 378/62 |
| 6,226,353 B1 | * | 5/2001 | Wilkins et al. | 378/98.11 |
| 6,394,650 B1 | * | 5/2002 | O'Hara et al. | 378/182 |

OTHER PUBLICATIONS

"Phase–contrast imaging using polychromatic hard X–rays," S.W. Wilkins, T.E. Gureyev, D. Gao, A. Pogany & A.W. Stevenson, vol. 384, Nov. 28, 1996.

"Mammography with Synchrotron Radiation," Emilio Burattini, PhD, Elsa Cossu, MD, Cosimo Di Maggio, MD, Mauro Gambaccini, PhD, Piero L. Indovina, PhD, Michele Marziani, PhD, Marco Pocek, MD, Sirio Simeoni, AT, Giovanni Simonetti, MD, vol. 195, No. 1, Apr. 1995.

"Single– and dual–energy CT with monochromatic synchrotron x–rays," F A Dilmanian, X Y Wu, E C Parsons, B Ren, J Kress, T M Button, L D Chapman, J A Coderre, F Giron, D Greenberg, D J Krus, Z Liang, S Marcovici, M J Petersen, C T Roque, M Shleifer, D N Slatkin, W C Thomlinson, K Yamamoto, and Z Zhong, Phys. Med. Biol. 42 (1997) 371–387.

X–Ray Microscopy in Biology and Medicine, ed. By K. Shinohara et al., Japan Sci. Soc. Press, Tokyo/Springer–Verlag, Berlin, pp. 193–202 (1990).

X–Ray Microscopy Proceedings of the International Symposium, Göttingen, Fed. Rep. of Germany Sep., 14–16, 1983, G. Schmahl and D. Rudolph.

"The Göttingen X–Ray Microscope and X–Ray Microscopy Experiments at the BESSY Storage Ring," D. Rudolph, B. Niemann, G. Schmahl, and O. Christ (1976).

"Construction of a Micro Zone Plate and Evaluation of Imaging Properties," P. Guttmann.

"Prospects and Problems in X–Ray Microscopy," J. Kirz, D. Sayre.

* cited by examiner

*Primary Examiner*—Drew A. Dunn
(74) *Attorney, Agent, or Firm*—Howard & Howard

(57) ABSTRACT

A new radiography method which utilizes contrast enhancement mechanisms with highly collimated X-ray beams without optics to achieve high imaging resolution and improve the time resolution is disclosed. This invention includes irradiating the object with an unmonochromatized beam, specifically highly collimated synchrotron radiation, and detecting an unmonochromatized beam image after the unmonochromatized beam has passed through the object. With compact design, a system for imaging an object with very high resolution, X-ray radiography with a wide range of X-ray sources, such as synchrotron radiation, without any sophisticated X-ray optics is also disclosed. This invention may achieve real-time images with micrometer resolution.

11 Claims, 3 Drawing Sheets

APPARATUS AND METHOD FOR IMAGING AN OBJECT WITH REAL-TIME RESPONSE

FIELD OF THE INVENTION

This invention relates to radiographic imaging and more particularly to a system and method for obtaining real-time images of an object with very high space and time resolution.

BACKGROUND OF THE INVENTION

In U.S. Pat. No. 5,850,425, an X-ray or neutron optic configuration includes a plurality of single crystal portions formed with respective spaced X-ray or neutron reflection faces formed at predetermined asymmetry angles to a Bragg diffraction plane in the respective crystal portion. The crystal portions are interconnected to maintain a first and second of these faces spaced apart for receipt of a sample between them and to allow small adjustments of the relative angle of the faces about the normal to the plane of diffraction while maintaining the normals to the Bragg planes for the first and second faces substantially in the plane of diffraction. A first face is arranged to be a monochromator and collimator with respect to X-rays or neutrons of appropriate wavelength incident reflected through the sample for receipt by the second face, which thereby serves as an analyzer face.

U.S. Pat. No. 5,850,425 also discloses a method of deriving an X-ray or neutron beam image signal of a sample comprising: directing an X-ray or neutron beam onto a first X-ray or neutron reflection face for reflection from that face through the sample to a second X-ray or neutron reflection face and thence to X-ray detection means, said reflection faces being interconnected such that a beam Bragg diffracted by the first face is at or near the correct angle of Bragg diffraction by the second face, said reflection faces being formed in respective single crystal portions at predetermined asymmetry angles to a Bragg diffraction plane in the respective crystal portion, wherein said first face is arranged to be a monochromator and collimator with respect to X-rays or neutrons of appropriate wavelength incident on said first face and reflected thereby through the sample for receipt by the second face said second face thereby serving as an analyzer face; and wherein the second face is well matched in angular acceptance to the angular divergence of the beam from the first face, or is of higher angular resolution.

The system of U.S. Pat. No. 5,850,425, includes a plurality of single crystal portions and means interconnecting the crystal portions located between the X-ray source and the detector. In order to convert a polychromatic beam into a monochromatic X-ray, the system has complicated single crystal portions and means interconnecting the crystal portions located between the X-ray source and the detector. Therefore, the system of U.S. Pat. No. 5,850,425 is very complicated, in particular in respect of a multiple reflection monochromator/collimator arrangement.

In the method of U.S. Pat. No. 5,850,425, since only a monochromatic beam extracted from the white beam is incident into an object, the flux of the beam passing through the object is a small amount and thereby the time necessary for imaging with X-rays is lengthened. Also, due to this reason, it is very difficult to obtain real-time images. Since the object of interests has to be exposed for a long time period in order to obtain an image with high resolution, the object is severely damaged.

On the other hand, in an other article, phase-contrast imaging using polychromatic hard X-rays, Nature 384: 335–338 (1996) by Wilkins S W, Gureyev T E, Gao D, Pogany A, Stevenson A W, a kind of optics pinhole is used. In this case, a polychromatic beam is used as an X-ray source. Since the pinhole is used as one element of the optics, the intensity of the X-rays is very low. For example, in the case that the distance between a specimen and a detector is more than 1 m, the exposure time is required to be about 60 minutes. Thereby there is a great limitation in obtaining high quality of real-time images. Also, when a sample such as live body is exposed for a long time, the sample is severely damaged.

U.S. Pat. No. 5,881,126 also discloses a phase-contrast X-ray imaging system comprising an X-ray interferometer, wherein X-ray interfering beams thicker than 2 cm☐2 cm are formed enabling observation of comparatively large objects. The X-ray interferometer is constituted by two crystal blocks each of which is monolithically cut out from ingots of crystal and have two wafers which function as X-ray half mirrors. Optical equipment, a chamber, and a feedback system are incorporated to adjust and stabilize the crystal blocks. A device is also incorporated to obtain an image showing the distribution of the X-ray phase shift with which diagnosis becomes easier and reliable. In the optical system a monochromatic beam is used as an incident beam. The flux of the beam becomes extremely low and thereby it is not possible to obtain X-ray images with nearly real-time response.

It was thought in prior arts, for example Burattini E, Di Maggio C, Gambaccini M, Indovina P, Maryiani M, Porek M, Simeoni S, Simonetti G (1994) Mammogrphy with Synchrotron Radiation. Radiology 125: 239–244, that, in order to obtain images with high resolution, a monochromatic beam has to be used. In the case of biological imaging, enhanced contrasts, i.e., DPA (dual-photon absorptiometry) and KES (K-edge substraction) effects are achieved by the use of high atomic number (Z) contrast agents. Such agents would also typically lead to increase in magnitude of peak shifts associated with phase-contrast imaging since the real part of the refractive index is also essentially proportional to Z. However, as contrast agents are used, cumbersome processes are needed. Refer to Dilmanian F A, Wu X Y, Kress J, Ren B, Button T M, Chapman D, Coderre J A, Giron F, Greenberg D, Krus D J, Liang Z, Marcovici S, Parsons E, Petersen M J, Roque C T, Shleiger M, Slatkin D N, Thomlinson W C, Yamamoto K, Zhong Z (1997) Single and Dual-Energy CT with Monochromatic Synchrotron X-rays. Phys. Med. Biol. 42:371–387. Moreover, so as to obtain the monochromatic beam, an additional optical system is needed.

X-ray contact microscopy (Shinohara, Ito and Kinjo, 1994; Kinjo et al., 1994), imaging microscopy (Schmahl et al., 1991; Guttmann et al., 1992) and scanning microscopy (Kirz, 1991, Williams et al., 1992) have already been developed and applied to observe hydrated biological specimens. However, none of these microscopies are applicable to three-dimensional observation of thick hydrated biological specimens. Also, the quality of obtained images is not always sufficient for medical diagnosis.

OBJECTS OF THE INVENTION

It is one object of the invention to provide a system and a method for obtaining a real-time image of an object with high space resolution.

It is another object of the invention to provide a system and a method of imaging a diagnostic object at low dose levels.

SUMMARY OF THE INVENTION

The invention accordingly provides, in a first aspect, an imaging system comprising: a source for emitting a collimated white beam; means for filtering out photon energies lower than a selected energy level in the collimated white beam, thereby producing an unmonochromatized beam to be irradiated on an object; and means for detecting an unmonochromatized beam image having passed through the object. Preferably, the imaging system further comprises a processor for obtaining an image of the object based on an output of the detecting means. The collimated white beam emitting source includes a synchrotron radiation source.

The invention provides, in a second aspect, a method for imaging an object comprising: a step of extracting a collimated white (unmonochromatized) beam from a source; a step of filtering out the photon energies lower than a selected energy level in the collimated white beam, thereby producing an unmonochromatized beam; a step of irradiating the object with the unmonochromatized beam and a step of detecting an unmonochromatized beam image which has passed through the object. The collimated white beam is preferably but not exclusively from a synchrotron radiation source. This invention is effective in diagnostic applications with a reduced dose.

BRIEF DESCRIPTION OF THE DRAWINGS

The invention will be further described, by way of example only, with reference to the accompanying drawings, in which.

DETAILED DESCRIPTION OF THE INVENTION

Embodiment

Figure 1:
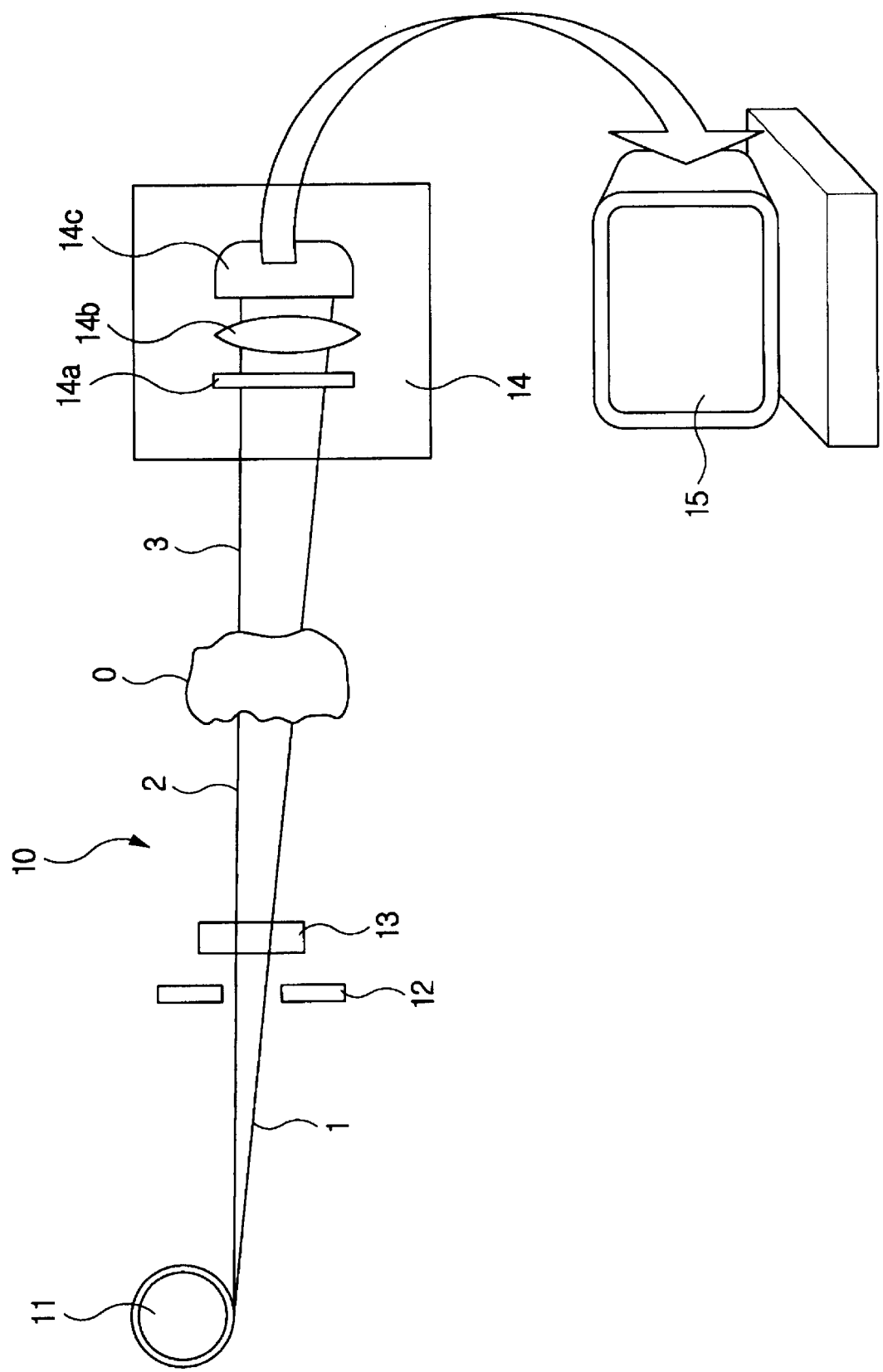
FIG. 1 is a simplified diagram of a simple X-ray imaging system in accordance with an embodiment of the first aspect of the invention.

The simple X-ray imaging system 10 depicted in FIG. 1 includes a collimated white beam generator 11. The generator is preferably but not exclusively a synchrotron radiation generator. Further components are a defining slit 12, a filter 13, a detector 14 and a computer 15. A defining slit 12 is positioned behind of the collimated white beam generator 11 in order to travel the collimated white beam 1 through the defining slit 12. The filter 13 is situated behind the defining slit 12. An object O is situated behind the filter 13. If necessary, an object stage may be arranged behind the slit 12 so as to hold the object O to detect in a position. The detector 14 is situated behind the object O in order to detect the beam passing through the object.

The detector 14 includes a CdWO4 single crystal scintillator 14a cleaved to a thickness of <100 □m—which is resistant to radiation damage and highly homogenous, an optical microscopy objective 14b with either 10× or 32× and a commercial-grade CCD video camera 14c.

The high-resolution radiograph on the scintillator is magnified with an optical microscopy objective with either 10× or 32×magnification, and captured by a commercial-grade CCD video camera.

The detector provided a good compromise between lateral resolution and high intensity (required for time resolution). It enables us to see details with a resolution of 2–3 □m, and to detect their evolution in real time, with a video rate of 30 image frames/sec.

In an other embodiment, the detector also may include a X-ray CCD camera. In particular, in the embodiments electronic imaging detectors such as those based on charge coupled devices (CCD's) may be used for high speed and, in some cases, real-time recording of images. A computer 15 is connected to the detector 14 in order to obtain an image of the object based on the output of the detector 14.

Now, a method of imaging an object will be described below.

A collimated white beam is generated by a source 11. The collimated white beam 1 is usually emitted from a synchrotron radiation source. In this embodiment, from the DB-beamline at the SRRC (Synchrotron Radiation Research Center, Hsinchu, Taiwan) 1.5 GeV storage ring and on the 1B2 beamline at PLS (Pohang Light source, Pohang, Korea), operating at 2.5 GeV is emitted a collimated white beam 1. The collimated white beam 1 is then introduced into a slit 12. The beam 1 travelling through the slit 12 is introduced into a filter 13. The filter 13 filters out photon energies lower than a selected energy level from the collimated white beam introduced into the filter 13, thereby producing an unmonochromatized beam 2. In this embodiment, the selected energy level of the collimated white beam is about 10 KeV. The collimated white beam filtered out by the filter 13, that is "an unmonochromatized beam" is irradiated into an object O.

Since longitudinal coherence is not a stringent requirement for refractive-index radiology, in this embodiment an unmonochromatized beam without any special optical element is used. At this time, the object O is placed on a beam path. The term "unmonochromatized beam" is defined herein as X-rays with a broad-band width photon energy distribution in which photon energies lower than a selected photon energy level are filtered out from a collimated white beam by a filter. Unmonochromatized beam image 3 having passed through the object O is detected by a detector 14, thereby providing an image. A scintillation crystal 14a included in the detector 14 serves to convert X-rays into visible rays. Image of the object O based on the output of the detector 14 is displayed on a monitor 15 or printed. This image may be saved in a computer or recorded on a video recorder.

Figure 2A:
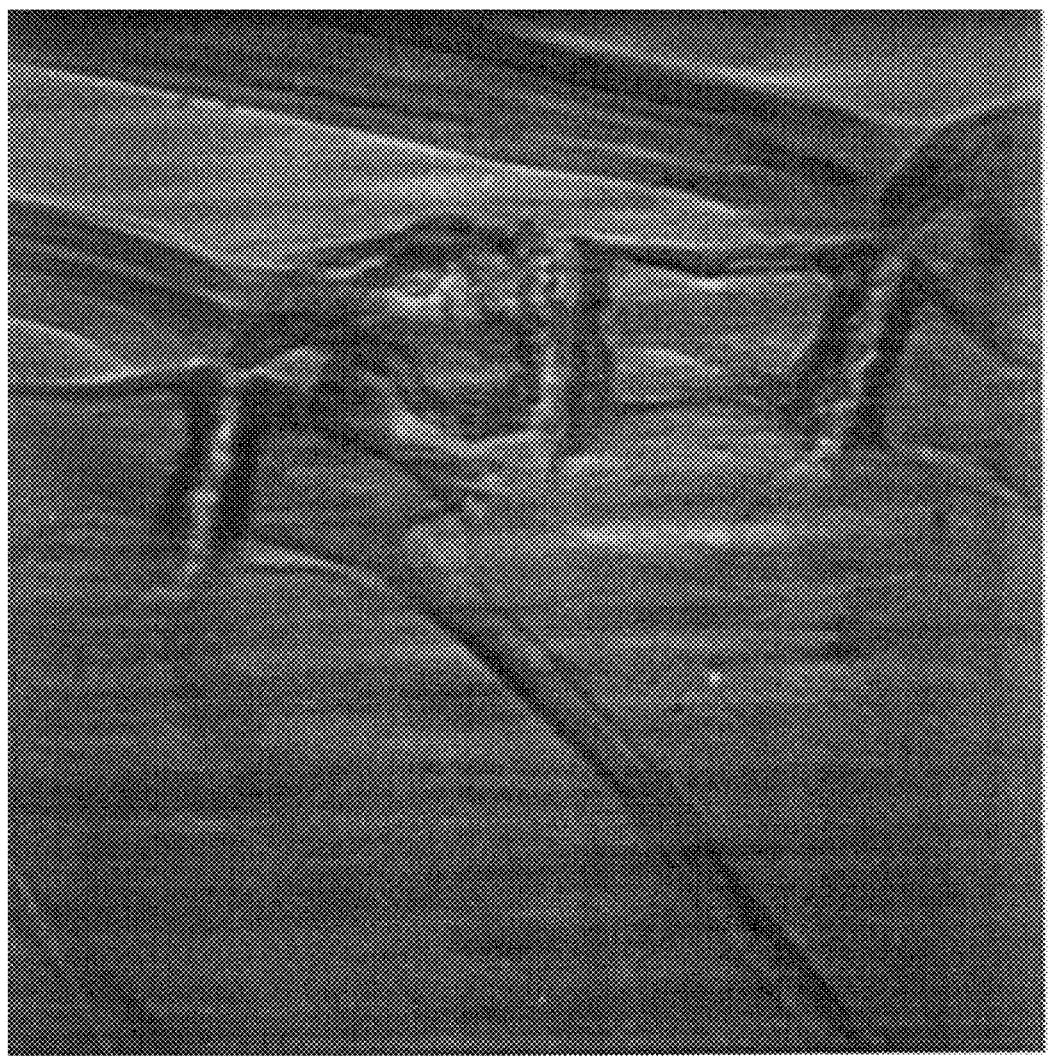
FIG. 2A is a radiograph of small fish taken with about 9 keV monochromatized X-ray photons.

FIG. 2A shows a radiograph of small fish taken with about 9 keV monochromatized photon beam according to a known technique. The object to the detector is 0.3 m.

Figure 2B:
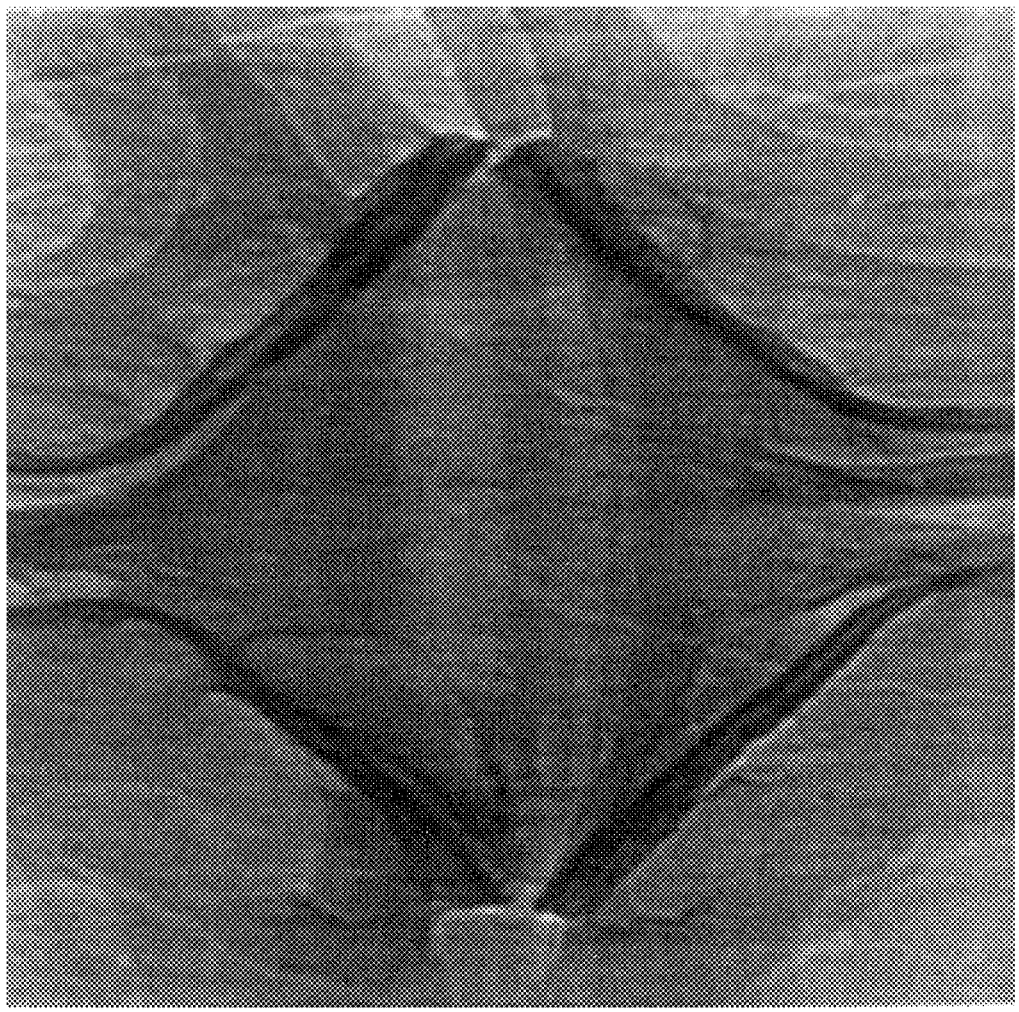
FIG. 2B is a radiograph of small fish taken with an unmonochromatized (white) photon beam.

FIG. 2B shows a radiograph of small fish taken with an unmonochromatized (white) photon beam in the embodiment according to this invention. The object to the detector is also 0.3 m.

The image of FIG. 2A was obtained with an monochromatized photon beam with about 9 keV photon energy and 10 sec. exposure whereas the image of FIG. 2B was obtained with an unmonochromatized (white) photon beam and 10 ms exposure per image. The field of view was 300 □m in both images.

From the two radiographs, it is noted that the image of FIG. 2B shows the same resolution but much shorter exposure than that of FIG. 2A. Therefore, according to this embodiment of this invention, it is possible to image an object with high resolution and real-time response without any damage to the object.

According to this invention, highly collimated and coherent X-ray sources provide an excellent solution to two major problems in radiography: poor contrast and poor lateral resolution. It is demonstrated that this solution can be implemented with high lateral resolution and fast time resolution, thereby opening the way to real-time microradiology investigations.

The key factor in this novel radiology approach is to achieve contrast by using the refractive index rather than absorption. The corresponding mechanisms can be either edge diffraction or edge refraction. A simple, relatively inexpensive and reliable experimental setup which enables to test the approach in real-time investigations is developed. It is also demonstrated that real-time microradiology is feasible with the majority of the present synchrotron sources.

A number of improvements that enhance our time-resolved approach are also considered and/or implemented. A lateral resolution of a few tenths of a micron can be expected by using a photoelectron-microscope-based detection technique. A better video camera would increase the number of pixels but possibly slow down the time per frame.

Such improvements would also decrease the total equivalent radioactive dose in view of medical applications. The situation is already quite interesting in that regard, since the possibility to operate on small areas with microradiology decreases by at least six orders of magnitude the equivalent does with respect to a conventional 200×200 mm$^2$ radiograph, taken with the same detection method and photon flux.

In conclusion, successful tests of real-time microradiology with collimated synchrotron radiation, using an unmonochromatized ('white') X-ray beam and a simple and effective detection system are performed. The advantages of time resolution are too evident to need further comments. In particular, preliminary tests on live specimens raise the possibility of novel diagnostic applications of microradiology as well as of a variety of applications in the life sciences.

The method for imaging an object according to the embodiments of this invention has the following benefits in contrast with those of prior art.
1. The image quality of radiography strongly depends on the quality of the optical element of the entire imaging system. The X-ray optics used to obtain "phase contrast" are typically difficult to make and to optimize. The deterioration of the optical properties of any of the X-ray optical elements in an optical path, will either greatly reduce the imaging quality or simply eliminate the "phase contrast" effect. This invention eliminates the necessity of using X-ray optics and can be applied to any small size collimated source.
2. This invention prevents the reduction in the X-ray intensity due to the X-ray optics.
3. This invention removes the necessity of using monochromatic X-ray for imaging.
4. This invention changes the photon energy spectrum that would be produced by absorbing optical elements, shifting its central photon energy to higher values.
5. According to this invention, a large fraction of the initial photon flux is used, thereby the time resolution and the lateral resolution are improved.

The range of potential applications of the proposed imaging systems and methods of this invention is vast. The range spans the fields of materials science, manufacturing industry, geology, biological, biomedical and clinical medicine.

In this disclosure, there is shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. A phase-contrast X-ray system for imaging an object, said system comprising:
   a source for emitting a collimated white beam;
   means for filtering out a photon energy lower than a selected energy level from the collimated white beam, thereby producing an unmonochromatized beam to be irradiated through the object, wherein a phase of the unmonochromatized beam shifts as the unmonochromatized beam irradiates through the object as a result of refractive index; and
   detecting means for detecting an unmonochromatized beam image having passed through the object by detecting shifts in the phase of the unmonochromatized beam as the unmonochromatized beam irradiates trough the object.

2. The phase-contrast X-ray system according to claim 1, further comprising a processor for obtaining an image of the object based on an output of the detecting means.

3. The phase-contrast X-ray system according to claim 1, wherein the collimated white beam emitting source includes a synchrotron radiation source.

4. The phase-contrast X-ray system according to claim 1, wherein the detecting means includes a scintillation crystal, an optical microscopy objective and a CCD camera.

5. The phase-contrast X-ray system according to claim 1, wherein the detecting means is an electronic imaging detector.

6. The phase-contrast X-ray system according to claim 5, wherein the electronic imaging detector includes a charge coupled device.

7. A method of imaging an object using a phase-contrast X-ray system, said method comprising the steps of:
   extracting a collimated white beam from a source;
   filtering out photon energies lower than a selected energy level from the collimated white beam, thereby producing an unmonochromatized beam;
   irradiating the object with the unmonochromatized beam such that a phase of the unmonochromatized beam shifts as the unmonochromatized beam irradiates through the object as a result of refractive index; and
   detecting an unmonochromatized beam image which has passed through the object by detecting shifts in the phase of the unmonochromatized beam as the unmonochromatized beam irradiates through the object.

8. The method in accordance with claim 7, further comprising processing an output of the detecting step in order to obtain an image.

9. The method in accordance with claim 7, wherein the collimated white beam is extracted from a synchrotron radiation source.

10. The method in accordance with claim 7, wherein the object is a thick hydrated biological object.

11. The method in accordance with claim 7, wherein the selected photon energy level is about 10 keV.

* * * * *